United States Patent
Saito

(10) Patent No.: US 8,746,884 B2
(45) Date of Patent: Jun. 10, 2014

(54) OPTICAL IMAGE ACQUISITION APPARATUS HAVING ADAPTIVE OPTICS AND CONTROL METHOD FOR THE SAME

(75) Inventor: Kenichi Saito, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/256,794

(22) PCT Filed: Apr. 8, 2010

(86) PCT No.: PCT/JP2010/056728
§ 371 (c)(1),
(2), (4) Date: Sep. 15, 2011

(87) PCT Pub. No.: WO2010/119915
PCT Pub. Date: Oct. 21, 2010

(65) Prior Publication Data
US 2012/0002165 A1    Jan. 5, 2012

(30) Foreign Application Priority Data

Apr. 13, 2009   (JP) ................................ 2009-097375

(51) Int. Cl.
*A61B 3/10* (2006.01)
*A61B 3/14* (2006.01)

(52) U.S. Cl.
CPC ........................................ *A61B 3/14* (2013.01)
USPC ......................................... 351/206; 351/205

(58) Field of Classification Search
USPC ........... 351/205, 206, 220, 221; 356/511, 512
See application file for complete search history.

(56) References Cited

U.S. PATENT DOCUMENTS

| | | | |
|---|---|---|---|
| 6,473,233 B1 * | 10/2002 | Iizuka | ........................... 359/566 |
| 6,634,750 B2 | 10/2003 | Neal et al. | |
| 6,890,076 B2 | 5/2005 | Roorda | |
| 7,118,216 B2 | 10/2006 | Roorda | |
| 2003/0038921 A1 | 2/2003 | Neal et al. | |
| 2003/0053026 A1 | 3/2003 | Roorda | |

(Continued)

FOREIGN PATENT DOCUMENTS

| | | |
|---|---|---|
| JP | 2000-352680 | 12/2000 |
| JP | 2005-501587 A | 1/2005 |

(Continued)

OTHER PUBLICATIONS

U.S. Appl. No. 13/260,452, filed Sep. 26, 2011, Kenichi Saito.

(Continued)

*Primary Examiner* — Mahidere Sahle
(74) *Attorney, Agent, or Firm* — Fitzpatrick, Cella, Harper & Scinto

(57) ABSTRACT

The present invention provides an optical image acquisition apparatus, while controlling the amount of light within the range prescribed by safety standards, etc., decreasing in image acquisition time by using a simple configuration, as well as securing a high resolution of an optical image by using adaptive optics.

Provided is an optical image acquisition apparatus having adaptive optics, the adaptive optics includes: a wavefront aberration detector for detecting a wavefront aberration in a reflected or backscattered beams generated when a plurality of beams are scanned on a surface, and a single wavefront aberration corrector for correcting a wavefront aberration in each of the plurality of beams, based on the wavefront aberration, and the plurality of beams enter the single wavefront aberration corrector with different incident angles and are overlapped on each other, and the wavefront aberration in each of the plurality of beams is corrected.

13 Claims, 8 Drawing Sheets

(56) References Cited

U.S. PATENT DOCUMENTS

2006/0087617 A1     4/2006    Roorda
2007/0247638 A1    10/2007    Owner-Petersen et al.
2012/0188506 A1*    7/2012    Zhou et al. .................... 351/205

FOREIGN PATENT DOCUMENTS

| JP | 2005-506107 A | 3/2005 |
| JP | 2005-224328 | 8/2005 |
| JP | 2006-094471 A | 4/2006 |
| WO | 02/075367 | 9/2002 |
| WO | 02/075367 A | 9/2002 |
| WO | 03/020121 | 3/2003 |
| WO | 03/020121 A | 3/2003 |
| WO | 2007/120112 | 10/2007 |

OTHER PUBLICATIONS

Hammer et al., "Compact Adaptive Optics Lines Scanning Laser Opthalmoscope", Proceedings of SPIE, Opthalmic Technologies XIX, vol. 7163, pp. 71630J-1-71630J-12 (2009).

Office Action issued in Korean Patent Office Application No. 10-2011-7026567, dated Apr. 15, 2013.

Office Action issued in Chinese Patent Office Application No. 201080016622.3, dated Mar. 5, 2013.

Daniel Hammer, et al., "Compact Adaptive Optics Line Scanning Laser Ophthalmoscope", Proceeding of SPIE, Feb. 18, 2009.

* cited by examiner

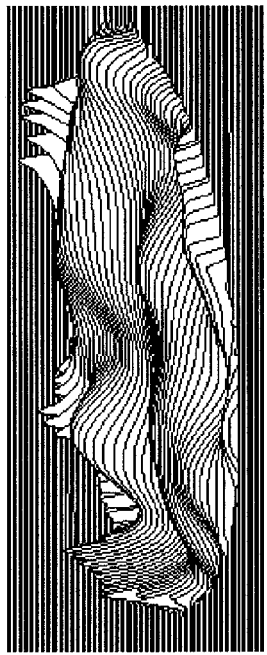
FIG. 3A
INCIDENT ANGLE 3.0°
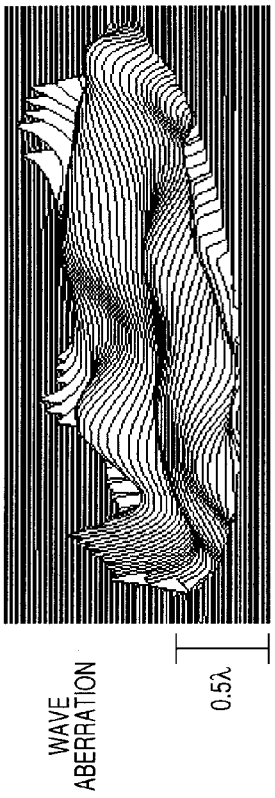
FIG. 3C
INCIDENT ANGLE 4.3°
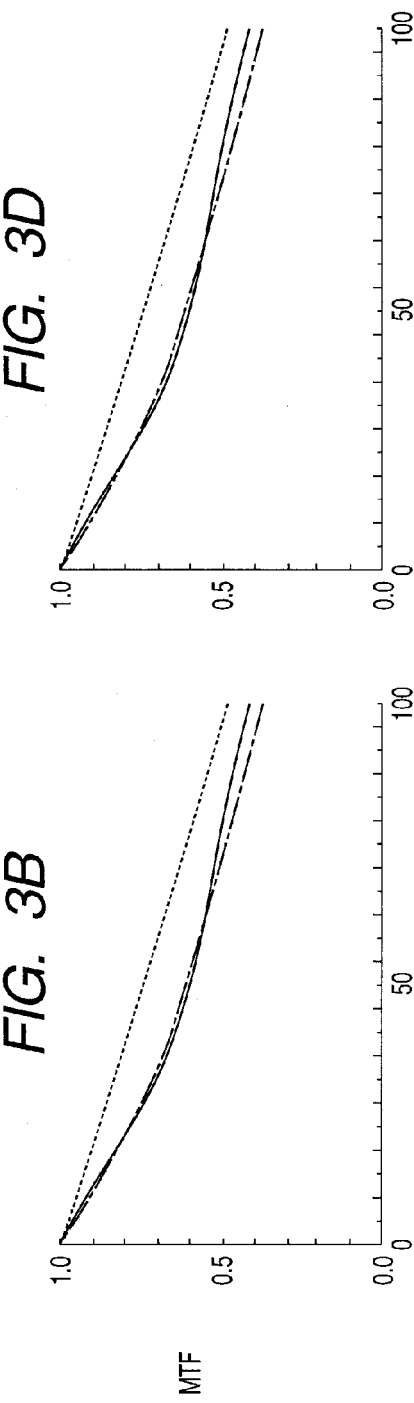
FIG. 3B
FIG. 3D

OPTICAL IMAGE ACQUISITION APPARATUS HAVING ADAPTIVE OPTICS AND CONTROL METHOD FOR THE SAME

TECHNICAL FIELD

The present invention relates to an optical image acquisition apparatus having adaptive optics and a control method for the same, and in particular to a technology by which a two-dimensional or three-dimensional optical image of a tissue in vivo including the retina in the eye which is an object can be acquired in a short time with a high resolution.

BACKGROUND ART

A known optical image acquisition apparatus for noninvasively acquiring an optical image of a tissue in vivo as an object such as the retina in the eye includes a Scanning Laser Ophthalmoscope (SLO) capable of acquiring a two-dimensional image, and Optical Coherence Tomography (OCT) capable of imaging a tomographic image of an object.

These apparatuses image and acquire a two-dimensional or three-dimensional optical image, by scanning the retina with a light beam using a deflector and measuring a reflected or backscattered beam. An OCT system includes Time Domain OCT (TD-OCT), Spectrum Domain OCT (SD-OCT) capable of imaging in a time shorter than TD-OCT, and Swept Source OCT (SS-OCT).

Further, regarding a technology for adaptive optics (AO) for acquiring a high resolution image, Japanese Patent Application Laid-Open No. 2005-224328 discloses the technology for correcting a wavefront aberration disturbed in the eyeball by using a wavefront aberration corrector. This is the image acquisition apparatus having an aberration correction function in which a single deformable mirror acts for multiple times on a single beam coming from an object to secure a necessary correction amount of aberration, and thereby a correction amount is secured.

DISCLOSURE OF THE INVENTION

However, in the apparatus having a wavefront aberration corrector through a single beam described above, even if a high resolution image can be provided, there is a problem with achieving decrease in image acquisition time. That is, if a scanning speed is raised for the speed-up, it becomes necessary to increase the amount of light to secure the S/N ratio.

At this time, if an object is an object like the retina in the eye, the quantity of allowable energy to be irradiated is restricted by safety standards, etc., not to injure the retina in the eye.

Because of the restriction of the quality of allowable energy to be irradiated in such a manner, the conventional embodiment through a single beam described above presents a problem with intending the speed-up by increasing the amount of light.

An object of the present invention, in view of the problem described above, is to provide an optical image acquisition apparatus capable of realizing decrease in image acquisition time by using a simple configuration, while controlling the amount of light used for scanning within the range prescribed by safety standards, etc., and securing a high resolution of an image by using adaptive optics, and a control method for the same.

The present invention provides an optical image acquisition apparatus having adaptive optics configured as follows.

The optical image acquisition apparatus of the present invention is an optical image acquisition apparatus having adaptive optics, in which reflected or backscattered beams reflected or backscattered by a surface to be measured which is an object when measuring beams including a plurality of beams are scanned on the surface are corrected by the adaptive optics, and providing an optical image of the object, wherein:

the adaptive optics includes:

a wavefront aberration detector for detecting a wavefront aberration in the reflected or backscattered beams generated by the object when the measuring beams including the plurality of beams are scanned on the surface to be measured, and a single wavefront aberration corrector for correcting a wavefront aberration in each of the plurality of beams, based on the wavefront aberration detected by the wavefront aberration detector, and the plurality of beams enter the single wavefront aberration corrector with different incident angles and are overlapped on each other, and the wavefront aberration in each of the plurality of beams is corrected.

Further, the control method of the present invention is a control method for an optical image acquisition apparatus in which a wavefront of reflected or backscattered beams reflected or backscattered by a surface to be measured which is an object when measuring beams including a plurality of beams are scanned on the surface is corrected, and acquiring an optical image of the object, characterized by comprising:

projecting the measuring beams including the plurality of beams on a single wavefront aberration corrector with different incident angles from each other, respectively, scanning the surface to be measured with the measuring beams reflected by the single wavefront aberration corrector by using a scanning unit, detecting a wavefront aberration in measuring beams reflected or backscattered by the surface to be measured by using a wavefront aberration detector, and controlling correction of the single wavefront aberration corrector, based on the detected wavefront aberration.

The present invention can realize an optical image acquisition apparatus capable of realizing decrease in image acquisition time by using a simple configuration, while securing a high resolution of an image by using adaptive optics, and controlling the amount of light used for scanning within the range prescribed by safety standards, etc., and a control method for the same.

Further features of the present invention will become apparent from the following description of exemplary embodiments with reference to the attached drawings.

BRIEF DESCRIPTION OF THE DRAWINGS

FIGS. 3A, 3B, 3C and 3D illustrates a wavefront and MTF after correction for illustrating dependency on an incident angle on a wavefront aberration corrector in a wavefront aberration correction performance in an exemplary embodiment of the present invention.

BEST MODES FOR CARRYING OUT THE INVENTION

Next, there is given a description of an optical image acquisition apparatus having adaptive optics in an exemplary embodiment of the present invention.

Figure 2A:
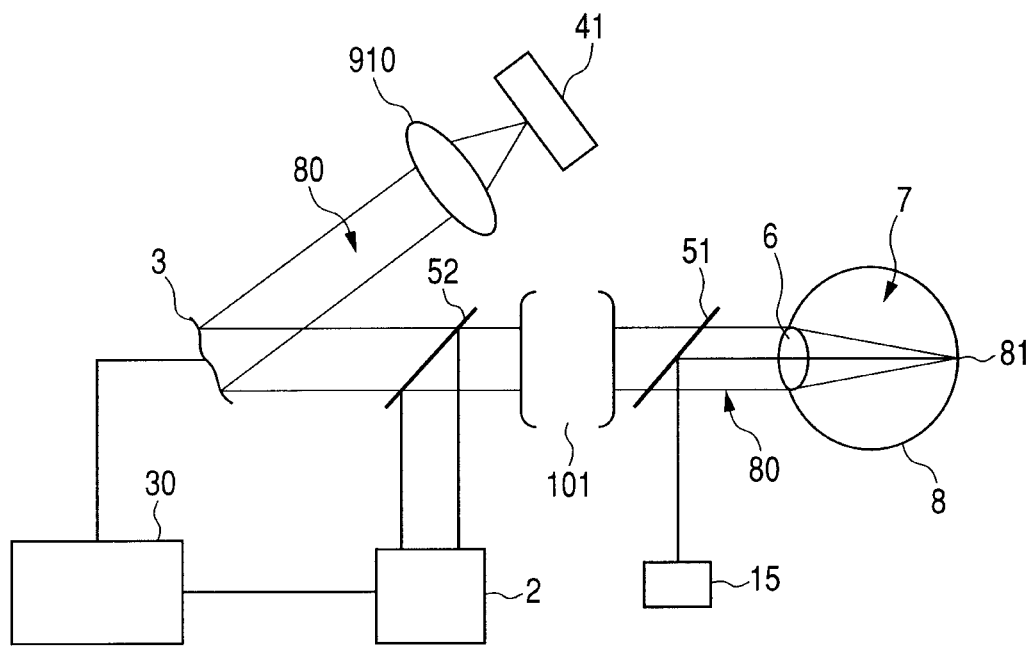
FIG. 2A illustrates a mechanism for realizing a high resolution of an image when a principle of adaptive optics (AO) is applied to a fundus inspection system.

Here, before details of the apparatus of the present exemplary embodiment are described, first, with reference to FIG. 2A, there is given a description of a mechanism for realizing a high resolution of an image when the principle of conventional adaptive optics (AO) described above is applied to a fundus inspection system.

To optically acquire information of the retina 8 in the eyeball 7, an illumination beam supplied from a light source 15 is irradiated to the retina, and a beam reflected or backscattered at a point 81 on the retina is adapted to form an image on a light receiving sensor 41 through optics 101 and 910.

This light receiving sensor 41, when it is a fundus camera, is an imaging device in which light receiving units are arrayed in a matrix, and, in SLO or OCT, corresponds to a optical fiber end leading to a light receiving element.

Here, when it is intended to acquire information with a high resolution, it is necessary to enlarge an entrance pupil of the optics 101, but, in such a case, because of an aberration contained in the eyeball, a beam 80 emitted from the eyeball has a wavefront disturbed. Hence, when an image from this beam is formed on the light receiving sensor 41 through the optics 101 and 910, an imaging performance which these optical systems originally have may not allow for light condense, and accordingly a disturbed and blurred spot is formed. Accordingly, a spatial resolving power in the lateral direction cannot be sufficiently provided, which does not allow for desired information with a high resolution.

This aberration includes some kinds of high-order aberrations such as a coma aberration and a fourth-order spherical aberration, in addition to some kinds of low-order aberrations which can be corrected by an ordinary optical device such as a cylindrical lens, such as an astigmatism, defocus and tilt.

These aberrations are produced from a deformation of a curved surface and/or inhomogeneity of a refractive index mainly of the anterior ocular segment such as the cornea and the crystalline lens. Because of a large difference between individuals and change in state of the tear layer over time, it becomes necessary to respond and correct from time to time.

The known adaptive optics (AO) described above is such that measures a generated wavefront aberration, and gives an aberration having opposite characteristics to cancel it, thereby carrying out correction.

This technology was originally developed as a method for correcting air fluctuation in real time to increase a resolving power when stars were observed with an astronomical telescope, and the method has been applied to the ophthalmic optical science.

A method widely used for detecting a wavefront aberration (the Shack-Hartmann system) is such that micro-lenses periodically arrayed in a matrix are disposed away from a light receiving surface of a two-dimensional imaging device by their focal length. Then, the amount of aberration is computed from a displacement of a spot condensed on the light receiving surface by each of the lens elements.

As a method for correcting a wavefront, a system is used in which mainly a shape of a reflecting mirror is changed. According to this method, a plurality of actuators are provided at the back of a thin, flexible mirror, and the mirror is locally pushed or pulled by using electrostatic power, magnetic force or a piezo element to change the whole shape of the mirror.

Further, a system is also known in which divided micro mirrors are moved in and out while being tilted. A local displacement magnitude is generally from a sub-micron to a dozen micron, and does not have an ability to change largely a focal length of an optical system. These devices are disposed at a position optically conjugate with the pupil 6 of the eyeball, and based on data detected by a wavefront aberration detector, a correction amount of a wavefront aberration corrector is computed and set. The results were reported that, according to this, two celestial objects whose images cannot be resolved without correction can be identified, and a distribution of visual cells in the retina can be provided.

In a configuration in FIG. 2A, in eyepiece optical system 101, a deformable mirror 3 (hereinafter called "DM3"), as a wavefront aberration corrector, is disposed at a position conjugate with an entrance pupil of the eyepiece optical system 101 (the pupil 6 of the eyeball).

Then, a Shack-Hartmann (HS) sensor 2, as a wavefront aberration detector, is disposed at a similarly conjugate position branched by a branching unit 52.

Here, a light source 15 for wavefront aberration detection is provided, and a beam from the light source enters the eyeball 7 through a branching unit 51, and is condensed on a point 81 on the retina 8.

A beam 80 reflected or backscattered at the point 81 is made by optics in the anterior ocular segment such as the cornea to be an approximately collimated beam, which passes through the branching unit 51 and is made by the optics 101 to be a beam having a predetermined thickness, and subsequently reflected by the branching unit 52, entering the HS sensor 2.

Figure 2B:
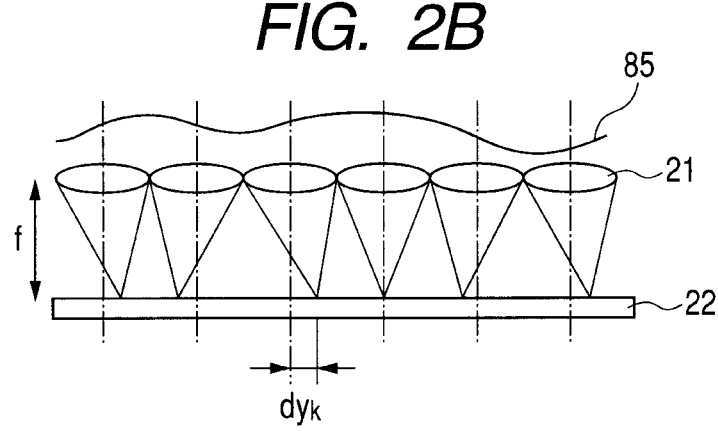
FIG. 2B is a conceptual diagram for illustrating a structure of an Hartmann-Shack wavefront sensor.

FIG. 2B illustrates a structure of the HS sensor 2 in a cross-sectional view.

Each portion of the incident beam which entered the HS sensor 2 passes through a sub-aperture of each of lens elements 21 in a micro-lens array portion disposed at a position optically conjugate with the pupil, and forms a spot on a two-dimensional imaging device 22 corresponding to each of the sub-apertures.

An image of the spot is formed at a position $dy_k$ shifted from an optical axis position of each of the micro-lenses on the imaging device (shown in dotted lines), depending on a slope of a wavefront 85 entering each sub-aperture. Let the focal length of the micro-lenses be f, then the slope $y_k$ of the wavefront is computed from $y_k = dy_k/f$. Now, let the number of micro-lenses be M, and let the number of actuators in DM3 be N, then a wavefront slope vector y and a correct signal vector a of DM3 may be expressed by the relation as follows:

$$y = [B] a \quad (1)$$

Where, $$y = \begin{pmatrix} y_1 \\ y_2 \\ \vdots \\ y_M \end{pmatrix}, a = \begin{pmatrix} a_1 \\ a_2 \\ \vdots \\ a_N \end{pmatrix}, B = \begin{pmatrix} B_{11} & B_{12} & \ldots & B_{1N} \\ B_{21} & B_{22} & \ldots & B_{2N} \\ \vdots & \vdots & \vdots & \vdots \\ B_{M1} & \ldots & \ldots & B_{MN} \end{pmatrix}$$

A matrix B shows an interactive relation between a wavefront slope magnitude and each of actuator correct signal values of DM3 for forming a wavefront slope magnitude.

The expression (1) ultimately expresses a wavefront aberration generated when the shape of DM3 changes. A value of each of elements in the matrix is determined dependent on how the shape of DM3 is changed according to the correct signal values, and this becomes different depending on a type of DM3. DM3 whose shape is changed by the divided mirrors as described above does not affect a surrounding, small region when some micro mirror is changed, but in a type whose shape is changed as a continuous surface, a surrounding small region is affected, and the value of B is determined based on that.

On the contrary, to acquire a correct signal value of DM3 for correcting a wavefront aberration detected by the HS sensor, the expression (1) may be inverse transformed, but an inverse matrix of B may not be generally obtained, and accordingly a pseudo inverse matrix $[B]^{-1}$, is used here. This may be expressed using a permutation matrix $[B]^T$ of B:

$$[B]^{-1} = [B^T B]^{-1} B^T$$

Where, $$B^T = \begin{pmatrix} B_{11} & B_{12} & \ldots & B_{M1} \\ B_{21} & B_{22} & \ldots & B_{M2} \\ \vdots & \vdots & \vdots & \vdots \\ B_{1N} & \ldots & \ldots & B_{MN} \end{pmatrix}$$

Therefore, when a measured wavefront aberration (a slope of a wavefront at each of sub-apertures) is y, an actuator correct signal value a of DM3 may be computed as follows:

$$a = [B^T B]^{-1} B^T y \quad (2)$$

The aforementioned illustrates a conceptual, computational procedure. Each of actual values will be determined based on the relation between a sub-aperture where a wavefront slope is detected by the HS sensor and a position of actuators of DM3.

Returning to the system in FIG. 2A, based on a value of y detected by the HS sensor 2 and computed by a computing unit 30, and a value of B preset according to characteristics of each of elements, the shape of DM3 is changed according to a value a derived from the expression (2).

If FIG. 2A illustrates a fundus camera, a beam reflected or backscattered at a point 81 on the fundus portion illuminated with the illumination beam from the light source 15 passes through the anterior ocular segment and the optics 101, subsequently has its wavefront corrected by DM3, and then is condensed by an imaging lens 910, forming an image on the light receiving sensor 41. In the case of SLO or OCT, the light receiving sensor 41, as described above, corresponds to the fiber end, and a beam emitted from the fiber end 41 connected to the light source travels via DM3 and through the optics 101 to enter the eyeball, being irradiated to the point 81 on the retina.

At this time, if DM3 is not driven, a condensed light spot on the retina is disturbed and blurred because of aberrations of the eyeball, but, here, due to correction by DM3, the spot is condensed according to a desired resolving power.

A beam reflected or backscattered at this point propagates back through a path of the irradiated beam, and travels through the anterior ocular segment, the optics 101, DM3 and the lens 910 to enter the fiber end 41 described above, and subsequently propagates through the fiber to be sent to a light sensor (not shown).

Also here, due to the correction by DM3, an imaging performance of a spot on the fiber end 41 is improved, and a good fiber coupling efficiency can be provided, and the S/N ratio of the resultant image is also improved.

Adopting the technology for correcting a wavefront aberration described above can realize a high resolution of an image, but in the case of a single beam similar to the conventional example, there is presented a problem with achieving decrease in image acquisition time which is the goal of the present invention.

That is, the present invention, as described above, addresses achievement of a high resolving power and realization of decrease in image acquisition time.

As described above, if a scanning speed of beam is increased, it is necessary to increase the amount of light to secure the S/N ratio, but in the case of a fundus inspection apparatus, the quantity of allowable energy to be irradiated per unit area of the retina is limited to avoid damage to the eye.

Figure 1A:
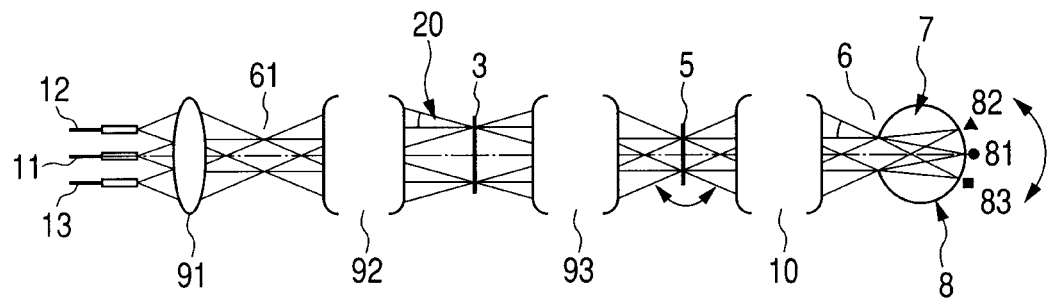
FIG. 1A is a conceptual diagram for illustrating a configuration of an optical image acquisition apparatus having adaptive optics and using a plurality of beams in an exemplary embodiment of the present invention.

The present inventors, to construct a system in which the amount of light described above is controlled within the upper limit value described above, have found adaptive optics in which a plurality of beams spaced apart from each other by a certain distance is irradiated to the retina, and which uses a plurality of beams as illustrated in FIG. 1A to scan each of divided areas at a time. The adaptive optics using a plurality of beams is adapted so that wavefront aberration correction of a plurality of beams is carried out by a set of a single wavefront aberration detector and a wavefront aberration corrector.

That is, because an aberration of the ophthalmological optics affects all of the plurality of beams described above, it becomes necessary to correct each of the beams when a beam having a thick diameter is used to realize a high resolving power.

At this time, if a wavefront aberration detector and a wavefront aberration corrector are provided by the number of beams to be projected, an optical system becomes large and also cost largely increases.

However, according to the configuration of the present invention described above, wavefront aberration correction of the plurality of beams is carried out by a set of a single wavefront aberration detector and a wavefront aberration corrector, allowing for a smaller optical system and a lower cost.

In such a manner, the configuration of the present invention described above can realize an optical image acquisition apparatus having adaptive optics capable of downsizing and reducing cost while not increasing the amount of incident light to the eye beyond a necessary level to raise a scanning speed of beams.

In FIG. 1A, three optical fiber ends 11-13 emit divergent beams, respectively, and the beams emitted therefrom are made by collimator optics 91 to be collimated beams, respectively, which enter a wavefront aberration corrector 3 through relay optics 92.

At this time, the respective beams enter with different incident angles, and coincide with each other on a surface of the wavefront aberration corrector 3, and here a wavefront of each of the beams is detected by a wavefront aberration detector (not shown), and corrected at a time by the single wavefront aberration corrector 3, based on the detected value. Subsequently, each of the beams is deflected by relay optics 93 and a deflector 5 such as a galvano-mirror and projected to the pupil 6 through eyepiece optical system 10.

The projected beams pass through the anterior ocular segment such as the cornea, and form spots 81, 82 and 83 on the retina 8 which is the surface to be measured, respectively, and are scanned in two-dimension.

At this time, without correction, an aberration contained in the ophthalmological optics disturbs the spots 81, 82 and 83, but here the wavefront aberration corrector 3 allows an image to be well formed, and thereby the spots are provided with a desired spot diameter.

Beams reflected or backscattered at these spots are emitted back from the pupil 6 through the anterior ocular segment, and enter the wavefront aberration corrector 3 through the eyepiece optical system 10—the relay optics 93, again.

These reflected or backscattered beams also have a wavefront aberration as the result of receiving the effect of an aberration contained in the ophthalmological optics, but the wavefront aberration is corrected by the wavefront aberration corrector 3 again and at a time.

Thus, the reflected or backscattered beams are well condensed on the fiber ends 11, 12 and 13 through the relay optics 92 and the collimator optics 91, respectively, and combined with the fibers with a high efficiency.

Here, scanning by using the three beams allows for a measurement three times faster without increase in the amount of incident light to the eye.

At this time, if there is a large difference in incident angle 20 between each of the beams entering the wavefront aberration corrector 3, a difference in correction result between each of the beams may be caused, and a phenomenon that cannot be well corrected may occur in some beam.

If the difference in incident angle exceeds about 5°, a reasonable level of degradation may be caused dependent on conditions.

However, for example, when the fundus is measured to acquire an image with a high resolution of several μm, a region on the retina data of which has to be acquired at a time may be a region having one side of about 1 mm to 2 mm.

It is because that attention is paid to a narrow region when an image is observed with a high resolution after acquiring the image. For example, let's consider the case where a square region having one side of 1.8 mm is divided into three regions in the direction parallel to the surface of FIG. 1A (called "y direction") to measure by using three beams as illustrated in FIG. 1A.

At this time, an area in charge of each of the beams in the y direction has the width of 0.6 mm, respectively, and a view angle corresponding to this is about 2.08°.

Here, let a beam entering the pupil have the thickness of 6 mm, and let an effective diameter of the wavefront aberration corrector be 10 mm, then the difference in incident angle between each of the beams entering the wavefront aberration corrector becomes about 1.25° with consideration for an angular magnification, and it is sufficiently small.

FIGS. 3A and 3C illustrate a correction residual of a wavefront aberration in two beams entering a wavefront aberration corrector (DM) with a difference in incident angle of 1.3° (incident angles of 3° and 4.3°, respectively), and FIGS. 3B and 3D illustrate MTF of each of the beams.

Here, the pupil is given an aberration on a wavefront aberration surface (including a third-order and fourth-order aberration) of an RMS value of about 0.3 μm, and an aberration is corrected by changing the shape of DM, based on a value acquired by the wavefront aberration detector regarding one of the beams (having the incident angle of 3°).

The beams entering the pupil have a beam diameter of φ4 mm, and DM has a continuous surface and an effective diameter of φ9 mm, and 37 actuators are disposed and arrayed in a hexagonal lattice.

From this result, it can be seen that the correction residual of both is small, and a difference in the result of MTF (Modulation Transfer Function) is also at a negligible level.

Further, a wavefront aberration produced in the ophthalmological optical systems is almost generated in the anterior ocular segment, and also a difference in incident angle between the beams entering the pupil is as small as about 2°, and therefore it can be determined that a difference between the wavefront aberration contained in each of the beams is also at a negligible level. According to the configuration of the present exemplary embodiment described above in which a plurality of beams are scanned, a good image having a high S/N ratio can be provided in a short time by using a single wavefront aberration corrector.

A configuration adapted so that a plurality of beams enter a single wavefront aberration corrector with different angles from each other, and coincide with each other may be the following configuration.

For example, a configuration can be adapted so that exit ends of a plurality of divergent beams are disposed at a front focus position of collimator optics 91 on a plane perpendicular to the optical axis, and thereby a principal lay of each of exit beams is parallel to the optical axis of the collimator optics 91.

These beams form an exit pupil 61 at a back focus position of the collimator optics 91, so that a wavefront aberration corrector 3 may be disposed at a position optically conjugate with the position of the exit pupil 61. This allows a plurality of collimated beams to enter with different angles and to arrive at the same position by using a common optical system.

Figure 1B:
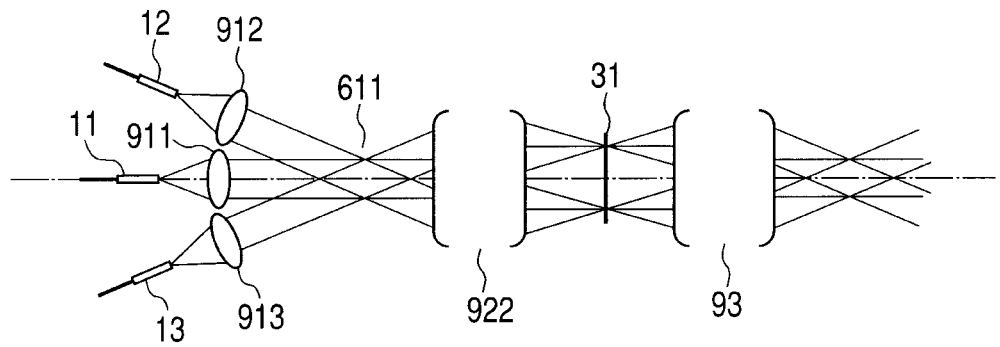
FIG. 1B illustrates an example of another configuration.

Also, another configuration may be as illustrated in FIG. 1B.

That is, a plurality of collimator optics 911, 912 and 913 are set up at exit ends of a plurality of divergent beams corresponding to each of the plurality of divergent beams.

The beams made collimated due to this configuration are adapted to intersect with each other at a single position 611 with a predetermined angle, and a wavefront aberration corrector 3 is disposed at a position of an exit pupil 31 formed by relay optics 922 whose entrance pupil is the intersection point.

The wavefront aberration corrector has been described above, and a configuration of a wavefront aberration detector is hereinafter described.

Generally, a wavefront aberration detector and a wavefront aberration corrector are disposed at a position optically conjugate with a position of a pupil of the entire optical system.

It is because that both of them detect and correct a wavefront aberration in a situation equivalent to that at a pupil.

If it is set up so that a plurality of beams enter a wavefront aberration corrector with different angles as described above, a plurality of beams also will enter similarly with different angles a wavefront aberration detector disposed at a position conjugate with a position of the wavefront aberration corrector.

In such a case, a plurality of beams are mixed in an HS sensor, so that it becomes difficult to correctly detect a wavefront aberration in each of the beams.

Figure 4:
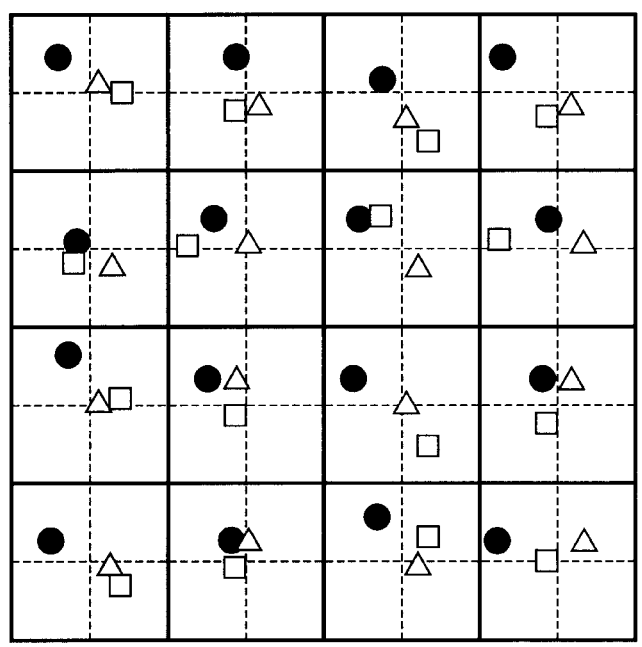
FIG. 4 illustrates a situation in which a plurality of beams enter a wavefront aberration detector to illustrate an exemplary embodiment of the present invention.

For example, if a detector is an HS type, a slope of a wavefront that enters each of sub-apertures illustrated in FIG. 2B differs between each of the beams, and accordingly a plurality of beams, as illustrated in FIG. 4, are formed in each of segments, and it cannot be determined which of the beams in each segment corresponds to which of the beams entering. In FIG. 4, a different mark designates a spot formed on a two-dimensional imaging device by a different beam.

Further, because a correct signal for a wavefront aberration in one of a plurality of beams can be provided as described with reference to the corrector, a configuration may be adapted to measure a wavefront aberration in at least one of the beams.

Figure 5A:
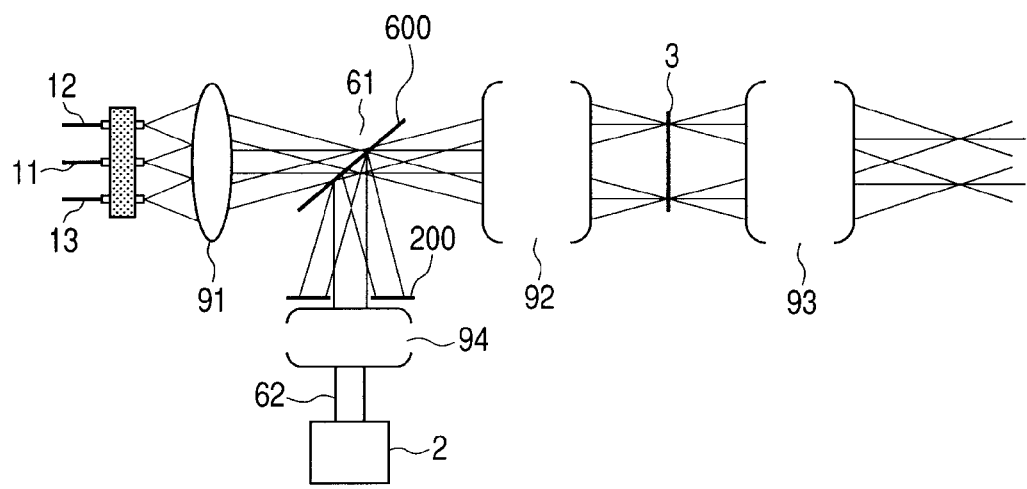
FIG. 5A illustrates one example of a wavefront aberration measurement in an exemplary embodiment of the present invention.

A first solution for the purpose, as illustrated in a conceptual diagram in FIG. 5A, has a configuration adapted to project only the beams desired to be measured to a wavefront aberration detector, and to block other beams from entering the detector.

Here, a light branching unit 600 is provided between collimator optics 91 and relay optics 92, and relay optics 94 forms an exit pupil 62 conjugate with an exit pupil 61 of the collimator optics 91, and a detecting surface of a wavefront aberration detector 2 is disposed at a position of the exit pupil 62.

Here, beams reflected or backscattered at spots 81, 82 and 83 on the retina (not shown) are reflected by the branching unit 600 through optics 93 and 92, and directed to the wavefront aberration detector 2 by the optics 94.

At this time, to prevent all beams except for the one from the point 81 entering the detector 2 as described above, a screen 200 is disposed at a position where a plurality of beams are separated, at the front, at the back, or inside of the optics 94.

Thus, only the beam reflected or backscattered at the point 81 on the retina, for example, enters the detector 2. Also, a wavefront aberration value acquired from this is used to form a signal to the wavefront aberration corrector, allowing a wavefront aberration in all beams to be corrected.

Further, if beams cannot be separated into their components due to a problem with, i.e. an angle between the beams, a method in a second solution is adopted that beams except the beam whose aberration is detected are extinguished intermittently, and an aberration is measured only at that timing.

Figure 5B:
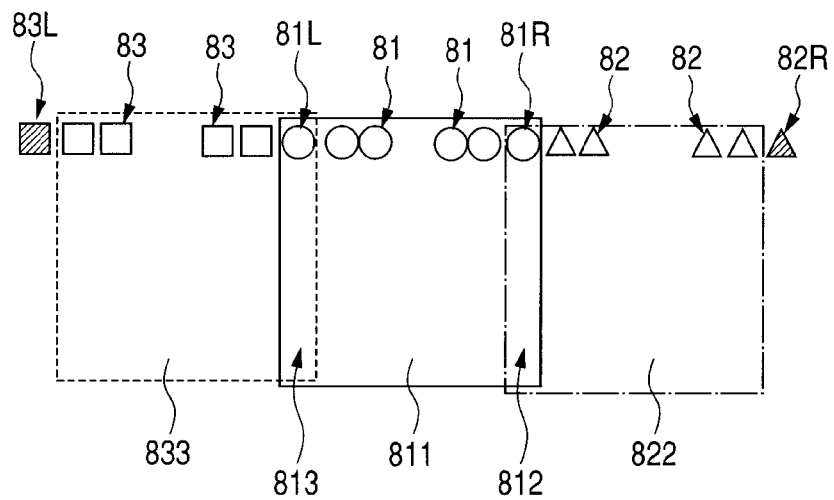
FIG. 5B illustrates, as another example, a wavefront aberration measurement according to time division.

As illustrated in a conceptual diagram in FIG. 5B, it is adapted so that a surface to be measured is divided into a plurality of small regions having an overlapped portion with an adjacent small region.

That is, when three divided regions 811, 822 and 833 are scanned with three beams (beams 81, 82 and 83), respectively, overlapped portions 812 and 813 are provided in boundary portions between adjacent regions.

When the three beams come to a right end of each of the regions, the beam 81 exists at a position 81R in the region overlapped portion 812, and the beam 82 exists at a position 82R outside of the region 822, and the beam 83 exists at a position 83R (the same position as a position 81L) in the overlapped portion 813. At this time, the beams 82 and 83 are extinguished and only the beam 81 continues to be lighted. While the beams 81 and 83 exist at the overlapped portions 812 and 813, respectively, this situation continues, and a wavefront aberration is measured by the wavefront aberration detector.

Also, on the contrary, when the three beams come to a left end of each of the regions, the beam 81 exists at the position 81L in the overlapped portion 813, and the beam 82 exists at a position 82L (the same position as the position 81R) in the overlapped portion 812, and the beam 83 exists at a position 83L outside of the overlapped portion 833.

At this time, similarly, the beams 82 and 83 are extinguished and only the beam 81 continues to be lighted. While the beams 81 and 82 exist at the overlapped portions 813 and 812, respectively, this situation continues, and a wavefront aberration is measured by the wavefront aberration detector.

While the beams exist except at these areas, all of the three beams enter the wavefront aberration detector, but at this time, a wavefront aberration is not measured.

In such a manner, it is adapted so that when a plurality of beams are scanned, only one of the plurality of beams is lighted and other beams are extinguished only for a period during which overlapped portions are scanned, and a measurement is made in time division.

This configuration allows for a measurement of a wavefront aberration in only one of a plurality of beams, and wavefront aberration correction by driving a wavefront aberration corrector based on a value of the measurement.

On the one hand, according to a wavefront detection method other than the HS system, for example, collimated beams branched for wavefront detection, as-are, are adapted to form an image on a two-dimensional imaging device through a lens.

Then, the method is such that a point spread function (PSF) on an image surface is acquired, and an inverse problem is solved, and thereby a wavefront is computed.

In such a case, also if a plurality of beams are detected, each of the beams forms an image at a particular position apart from each other, and it can be identified to which of the observed beams the image corresponds.

If an incident angle on a wavefront aberration corrector is large, or if an aberration in an optical system is large, a wavefront of a single beam is measured, and based on the resultant data, a correction is made by a wavefront aberration corrector, so that a correction residual of the measured beam can be minimized, but other correction residual becomes large. On the contrary, as described above, aberrations of a plurality of beams are detected, and a wavefront is computed from PSF which averages these aberrations, and a driving signal of a wavefront aberration corrector is formed, so that a target value of wavefront correction becomes an average of a wavefront of each of the beams, and thereby a difference in wavefront correction residual between the beams can be reduced.

A case when a thick beam of 3 to 7 mm is projected on the eyeball to achieve a high resolving power of about several μm has been considered in the aforementioned.

However, in the case of the eyeball having a disease such as the cataract, even if a thick beam is projected, the beam is blocked by the affected part, and accordingly there can be provided a resolving power substantially equivalent to that provided when a thin beam is projected.

Further, only a part of the beam can pass through, and the amount of the incident light which arrive at the retina is lowered, and also a reflected or backscattered beam is reduced, and accordingly the S/N ratio of an image is ultimately decreased.

To prevent this, in the present invention, a zoom mechanism for varying a diameter of a beam entering the eyeball is provided between a plurality of light exit ends and a light deflector.

Then, dependent on conditions of the eye to be inspected, a value of a beam diameter can be varied, and according to the value of the beam diameter, wavefront aberration correction drive is turned on or off.

For example, when a region through which a beam unaffected by the cataract can pass is small, a thin beam having an entrance beam diameter of about 1 mm is projected to measure.

At this time, because of the thin beam, an effect received from an aberration in the ophthalmological optics can be considered almost negligible, and thus wavefront aberration correction is not needed, then turning a correction function off.

In such a manner, it is adapted so that only when a magnification of zoom optics is set to a predetermined magnification, wavefront aberration correction can be carried out by a wavefront aberration corrector, and thereby a computational load on a controlling unit can be reduced, so that it can be expected to execute signal processing at a higher speed.

Because of the thin beam diameter, the resultant resolving power is about 20 μm which is a conventional level, but a resolving power can be secured to the degree of the diffraction limit essentially provided, and a good signal S/N ratio can be secured, allowing for addressing also the case of the eye having a bad condition.

Figure 6A:
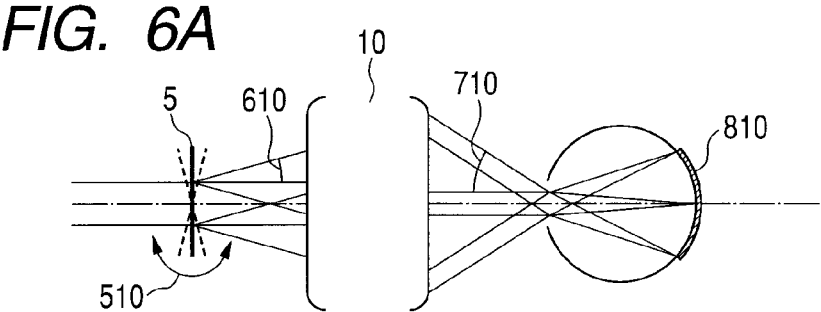
FIGS. 6A and 6B illustrate a concept of zooming of eyepiece optical system.

Also, a thinner beam diameter decreases a lateral magnification, and an angular magnification, as illustrated in FIG. 6A, is inversely increased, so that a wide region 810 on the retina can be observed at a time with a wide view angle 710.

Here, for the simplicity, the case where a single beam is scanned is illustrated.

Figure 6B:
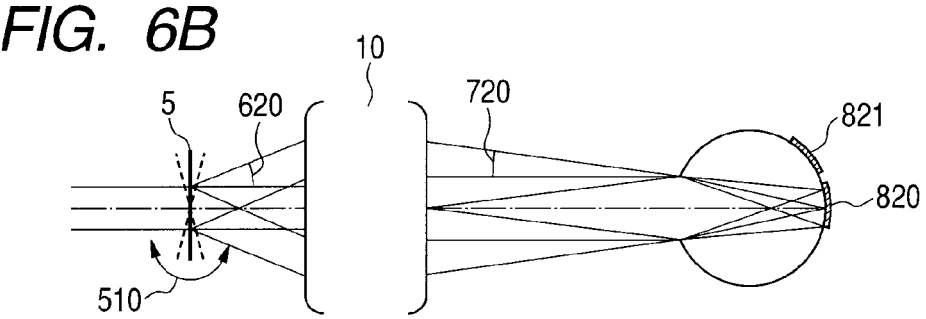

At this time, if eyepiece optical system 10 on the eyeball side of a deflector 5 has a zoom function, and inversely a thicker beam diameter, as illustrated in FIG. 6B, decreases an angular magnification, then a view angle 720 of the eyepiece optical system 10 is limited to a narrow angle in the vicinity of the optical axis.

Accordingly, a region 820 which can be observed is also limited to a narrow region in the vicinity of the visual axis.

If also a region 821 other than the region 820 is adapted to be observed, a deflection angle 510 of the deflector has to be increased, but it is difficult to provide a large deflection angle in a high-frequency area using a compact galvano-mirror, and accordingly a polygon scanner, etc. becomes necessary, resulting in a large apparatus.

Further, an angle of field 620 on the side of the deflector in FIG. 6B also becomes larger than an angle of field 610 on the side of the deflector in FIG. 6A, resulting in large eyepiece optical system 10 and also more difficult design.

Figure 6C:
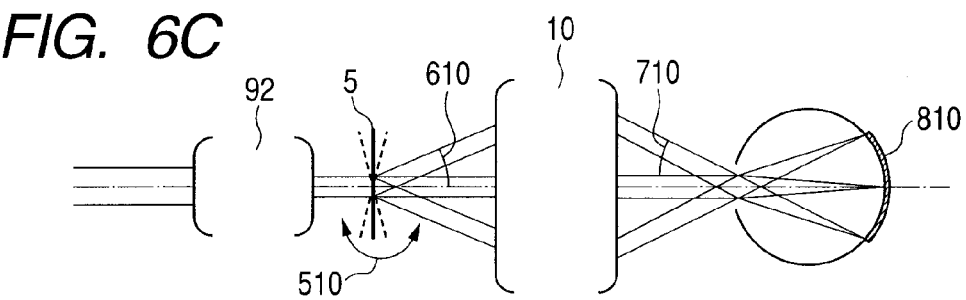
FIGS. 6C and 6D illustrate an example of a configuration in which zoom optics is disposed between a beam exit end and a deflector in an exemplary embodiment of the present invention.

However, because, in such a manner, a desired position cannot be enlarged and observed with a high resolution, zoom optics 92, as illustrated in FIG. 6C, is disposed between the deflector 5 and a beam exit end (not shown), and eyepiece optical system 10 is a fixed focus system.

Figure 6D:
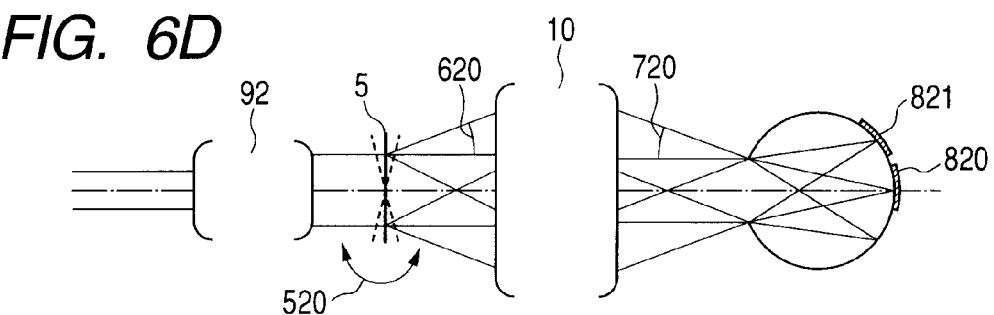

Accordingly, even when a lateral magnification of the optics 92 is increased to thicken a beam diameter, a desired position, as illustrated in FIG. 6D, can be appointed to provide an enlarged, observed image if secures an angle of field 620 in the eyepiece optical system 10 is secured for this thickened beam.

However, in a system in which a plurality of beams are simultaneously scanned, when a lateral magnification of a zoom system is increased to set a high resolving power mode, a beam spot on the retina is reduced, and at the same time beam spacing is also reduced with the same ratio, and thus an angle at which each of beams is scanned is also reduced and limited.

It is because that an adjacent beam region is doubly scanned if scanned at an angle beyond this angle.

Therefore, in fact, a region which can be observed is limited to a reduced, narrow range 820, but a deflection angle 520 of a deflector required at this time is small and the maximal deflection angle of the deflector and the maximal angle of field of the eyepiece optical system 10 are larger, compared to their actual angles.

Therefore, if a scanning timing is shifted, a region 821 outside of the optical axis can be observed.

In this system, if a wavefront aberration corrector is disposed on the deflector side of zoom optics 92, and a lateral magnification of the zoom optics is decreased to thin a beam diameter, then an angular magnification is increased and a difference in incident angle between each of beams entering the wavefront aberration corrector is increased.

Then, as described above, it becomes difficult to correct well a wavefront aberration in each of a plurality of beams at a time. Also at this point, in the mode of a thin beam and a wide angle of field, a wavefront aberration correction function is desirably turned off.

Therefore, it is set up so that when a beam having a diameter of more than 2.5-3.0 mm on which an aberration in the ophthalmological optics has an effect is used, wavefront aberration correction drive is carried out, but when the beam diameter is less than that, the correction is not carried out.

However, the clause "wavefront aberration correction drive is not carried out here" means that an effect on a wavefront imposed by the wavefront aberration detector is reduced to zero, and includes the case where, for example, in the case using DM, the wavefront aberration correction is driven with a driving signal to force a DM surface to be planar if the DM surface does not become planar at zero of the driving signal. Also, when the beam diameter is changed by the zoom function described above, a diameter and/or an incident angle of a beam entering the wavefront aberration detector or the corrector is changed dependent on a setup, and the number of sub-apertures of the detector and/or the number of actuators of the corrector cannot be sufficiently exploited, and therefore correction with a necessary precision may not be provided.

To avoid this, the zoom optics is installed on the eyeball side (on the side of an object) than the wavefront aberration detector and the wavefront aberration corrector.

Thus, even when zooming is applied, a beam entering both of them becomes constant, and a correction precision always having the same condition can be secured.

EMBODIMENTS

Embodiments of the present invention are hereinafter described.

Exemplary Embodiment 1

Figure 7:
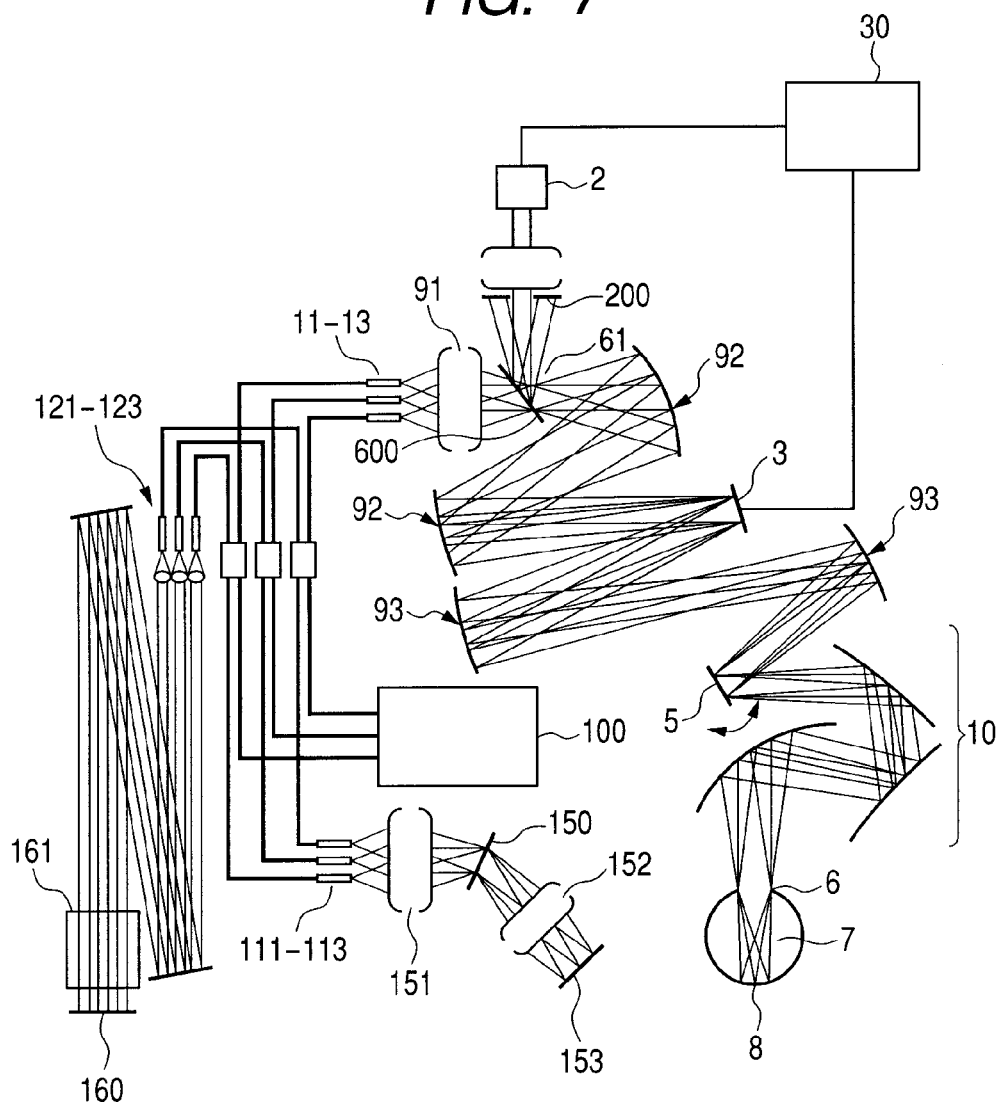
FIG. 7 illustrates an example of a configuration in which adaptive optics in a first exemplary embodiment of the present invention is applied to OCT.

A first exemplary embodiment describes an example of a configuration with reference to FIG. 7 in which the adaptive optics of the present invention described above is applied to OCT capable of acquiring a three-dimensional optical tomographic image.

A beam emitted from a low-coherence light source 100 propagates through an optical fiber and is branched with a predetermined ratio by a fiber combiner, and subsequently is emitted as a divergent beam (measuring beam) from exit ends 11-13, respectively, and then made collimated by collimator optics.

The three beams made collimated pass through an exit pupil 61, pass through relay optics 92 including a curved mirror, and subsequently enter, in the state of collimated beams with different incident angles, DM3 which is a surface optically conjugate with the pupil 6 in an inspected eye and the exit pupil 61, and then are overlapped on the DM surface with each other. At this time, a beam diameter of each of the beams is φ10 mm, and approximately equal to an effective diameter of DM3. At this time, a correct signal is not sent to the DM surface, and it is planar.

A beam reflected thereby is also made collimated by relay optics 93, and enters a deflector 5 (galvano-mirror) with different angles.

The galvano-mirror 5 has mirrors having a different rotation axis disposed close to each other therein. The beam deflected thereby is projected on the pupil 6 in the eyeball 7 in a collimated beam by eyepiece optical system 10, and scanned on the retina 8 in two-dimension. Because a beam spot at this time has its wavefront disturbed by an aberration contained in the eyeball, the beam spot is disturbed and blurred.

Beams reflected or backscattered at the three spots condensed on the retina are emitted from the pupil 6, and propagate back to the eyepiece optical system 10—the relay optics 92, subsequently are reflected by a light branching unit 600, and then enter an HS sensor 2.

At this time, on the HS sensor, only the beam reflected or backscattered by the retina and formed of the beam from the light exit end 12 is projected, and then reflected or backscattered beams formed of other beams are blocked by a light blocking unit 200 not to enter the HS sensor.

Based on a measured value by the HS sensor, a correct signal to DM3 is computed by a computer 30 and sent to DM3. A shape of DM3 is changed according to this signal to correct a wavefront aberration.

Thus, a wavefront of each of the beams from the light exit ends 11-13 is changed, and each of the spots on the retina is corrected and to be at a state near the diffraction limit.

In this embodiment, a diameter of the beams entering the pupil 6 is set to about 4 mm, and a spot diameter on the retina becomes about 5 μm.

Further, the reflected or backscattered beam at each of the spots is given a wavefront aberration again when it passes through the ophthalmological optics, but a disturbed wavefront is corrected by DM3, and thereby the beam forms a good image on each of the fiber exit ends 11-13 through the relay optics 92 and collimator optics 91.

Then, the beam enters each of the fibers with a high coupling efficiency.

On the one hand, similarly, the beam emitted from the light source 100 is branched by the fiber coupler with a predetermined ratio, and subsequently emitted from each of exit ends 121-123 on the side of a reference arm.

Then, the beam is made collimated by collimator optics, and subsequently enters each of the exit ends 121-123, again, through a dispersion compensation glass 161 and a folding mirror 160.

A reference beam travelling through a reference light path and the reflected or backscattered beam by the eyeball described above are combined with each other by the fiber coupler to form an interference beam, which is emitted from each of exit ends 111-113 on the side of a spectroscope.

A divergent beam emitted therefrom is made collimated by collimator optics 151, and subsequently enters a diffraction optical element 150 to be diffracted.

Here, an incident angle is set so that a diffraction efficiency of a first-order diffraction beam is maximized.

A beam diffracted here is separated into its wavelength components, which are condensed on a detector 153 by imaging optics 153, but on the detector 153, an image is formed in the direction parallel to the plane of FIG. 7 at a different position for each of wavelengths.

In FIG. 7, a light flux of only the central wavelength is illustrated for the visibility.

Interference fringes are formed due to a light intensity distribution of an image formed on the detector 153 at a different position for each of wavelengths, and detected, and subsequently this signal is Fourier transformed to derive the relation between a position in the depth direction and a reflection factor, and then the beam is scanned on the retina in one dimension, and thereby a cross-sectional image thereof can be provided. Further, scanning in two-dimension also allows for a three-dimensional image.

Because the three beams are used here, a measurement can be made three times faster, compared to the case of using one beam, and at the same time an optical resolving power of 5 μm in the horizontal direction can be secured.

Exemplary Embodiment 2

Figure 8:
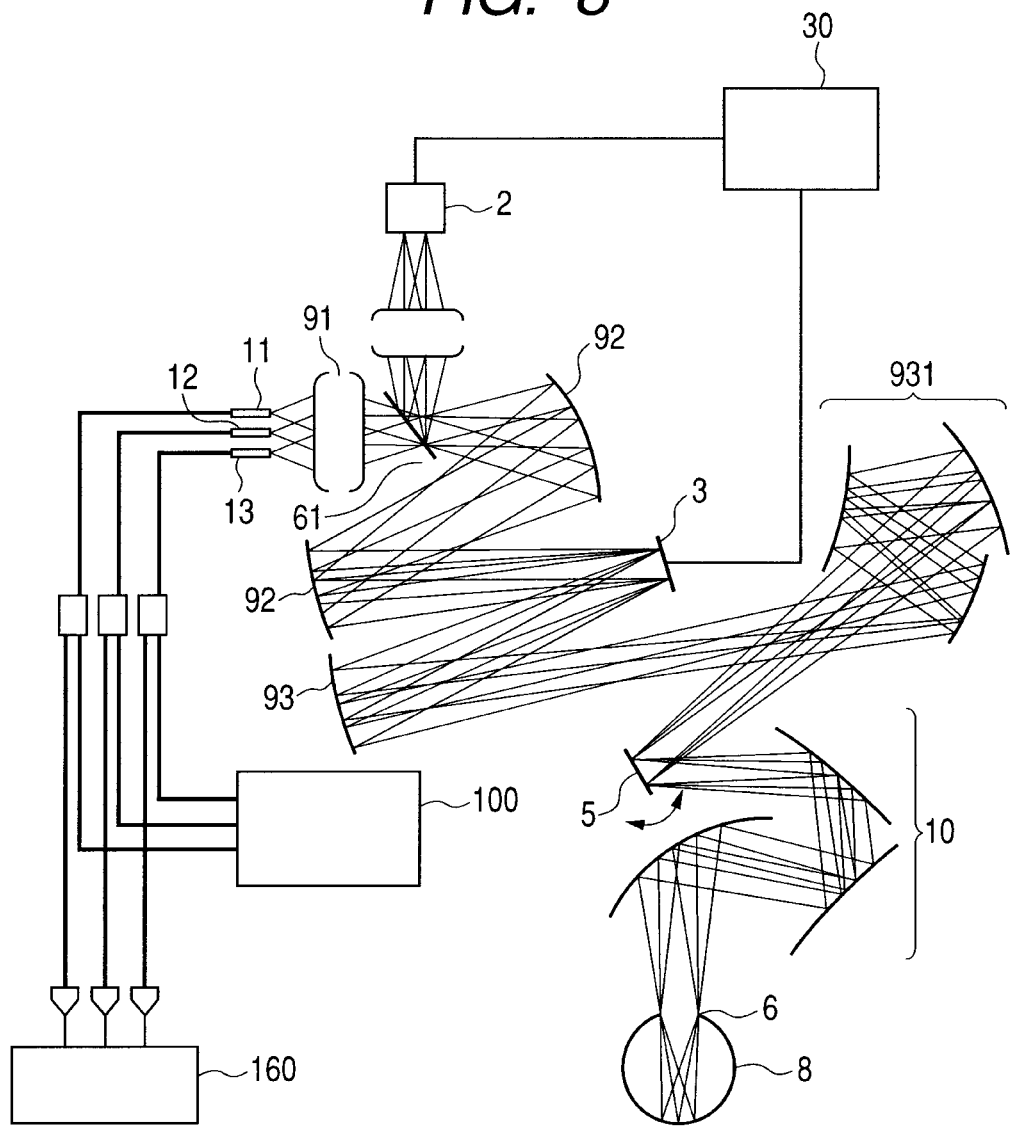
FIG. 8 illustrates an example of a configuration in which adaptive optics in a second exemplary embodiment of the present invention is applied to SLO.

A second exemplary embodiment describes an example of a configuration in which the adaptive optics of the present invention described above is applied to SLO capable of acquiring a two-dimensional image with reference to FIG. 8.

Because SLO, different from OCT, does not include an interferometer, SLO is a system in which light intensity of a beam reflected or backscattered by the retina is directly detected by a light intensity detector 160, and thereby a two-dimensional image is provided.

A configuration including fiber exit ends 11, 12 and 13 to eyepiece optical system 10 may be basically similar to those of the first exemplary embodiment.

An example in FIG. 8 has also a configuration common to the example in FIG. 7, but before an HS sensor, a beam light blocking unit is not included here, and all beams enter.

As described with reference to FIG. 5B, beam spacing and a deflection driving angle of a deflector are set so that a scanning range of each of beams has an overlapped portion with each other, respectively.

When the beams arrive at these overlapped portions, beams emitted from fiber exit ends 11 and 13 are extinguished in a light source 100, and only the reflected or backscattered beam through a fiber exit end 12 is measured.

When a region of 1.5 mm on the retina in the horizontal direction is measured at an entrance beam diameter of 7 mm, three beams scan divided regions, and accordingly each of the divided regions has the width of 0.5 mm, and a view angle at which the region is scanned is about 1.73°.

If eyepiece optical system has a pupil magnification of 1, a deflection angle of the deflector is 0.87°. At this time, to form an overlapped portion of 0.1 mm, respectively, between the three regions in FIG. 5B, i.e. between the regions 811 and 822, and between the region 811 and 822, the deflection angle of the deflector may be set to 1.21°.

Further, to be capable of addressing the case of the eye having a disease, zoom optics 931 for changing a beam diameter is provided between DM3 and the deflector 5.

By moving two of three mirrors in the optical axis direction, a diameter of a beam entering the deflector 5 can be changed from 1 mm to 7 mm.

On the one hand, the eyepiece optical system secures a performance in which an angle of view can reach 30° at an entrance pupil and an exit pupil of 7 mm. Therefore, at a beam diameter of 1 mm, a region having the width of 8.7 mm is scanned by the three beams whose scanning widths are 2.9 mm, respectively.

At this time, if the overlapped portion having the width of 0.5 mm is secured, the deflection angle of the deflector is 6.74°. At this time, the wavefront aberration correction is turned off to measure.

These allow for a measurement of a measured object in a short time while deflecting the diameter of the beam entering the eyeball dependent on conditions of the eyeball.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-097375, filed Apr. 13, 2009, which is hereby incorporated by reference herein in its entirety.

The invention claimed is:

1. An optical image acquisition apparatus for generating at least an image of an object using return beams returned from the object irradiated by a plurality of measuring beams, said optical imaging apparatus comprising:
    a single wavefront aberration obtaining unit configured to obtain wavefront aberration in the return beams; and
    a single wavefront aberration correcting unit configured to correct wavefront aberration in each of the return beams, which enter the wavefront aberration correcting unit with different angles, based on the obtained wavefront aberration,
    wherein the wavefront aberration obtaining unit is disposed at a position optically conjugate with that of the wavefront aberration correcting unit, and obtains a wavefront aberration in one beam of the plurality of return beams, and
    wherein the wavefront aberration correcting unit corrects wavefront aberration in each of the return beams based on the obtained wavefront aberration in the one beam.

2. The optical image acquisition apparatus according to claim 1, further comprising:
    a plurality of collimator optics configured to be provided corresponding to an exit end of each of the plurality of beams, wherein the plurality of beams emitted from the exit ends and made collimated by the plurality of collimator optics intersect with each other at a single position, and
    wherein the wavefront aberration correcting unit is disposed at a position at which an exit pupil of relay optics is acquired optically conjugate with the single position at which the plurality of beams intersect with each other.

3. The optical image acquisition apparatus according to claim 1, wherein:
    one collimator optics common to an exit end of each of the plurality of beams is provided, and the exit end of each of the plurality of beams is disposed on a plane perpendicular to the optical axis at a front focus position of the collimator optics,
    an exit pupil is acquired at a back focus position of the collimator optics through the plurality of beams emitted from the exit ends and made collimated by the collimator optics, and
    the wavefront aberration correcting unit is disposed at a position of an exit pupil of relay optics which is acquired at a position optically conjugate with the exit pupil acquired at the back focus position of the collimator optics.

4. The optical image acquisition apparatus according to claim 1, wherein:
    the wavefront aberration obtaining unit obtains a wavefront aberration in one beam of the plurality of return beams, and is configured to block the other beams of the plurality of return beams.

5. The optical image acquisition apparatus according to claim 1, wherein:
    the wavefront aberration obtaining unit obtains a wavefront aberration in one beam of the plurality of return beams, and
    when the object has a plurality of small regions including an overlapped portion with an adjacent portion, one beam of the plurality of measuring beams is lighted and other beams are extinguished while the overlapped portion is scanned by the plurality of measuring beams.

6. The optical image acquisition apparatus according to claim 2, further comprising:
    a deflector disposed between the exit ends of the plurality of beams and the object, and
    zoom optics disposed between the exit ends of the plurality of beams and the deflector and adapted to vary a lateral magnification,
    wherein only when the magnification of the zoom optics is set to a predetermined magnification, wavefront aberration correction by the wavefront aberration correcting unit can be carried out.

7. The optical image acquisition apparatus according to claim 6, wherein the zoom optics is disposed on the side of the object than the wavefront aberration obtaining unit and the wavefront aberration correcting unit.

8. The optical image acquisition apparatus according to claim 2, wherein:
    the exit ends of the plurality of beams are optical fiber ends, and
    by using an interference beam, between (i) a beam reflected or backscattered by the surface to be measured and returned to the optical fiber end and (ii) a reference beam acquired differently through another reference light path, a tomographic image of the object is acquired.

9. The optical image acquisition apparatus according to claim 2, wherein:

the exit ends of the plurality of beams are fiber ends, and reflected or backscattered beams returned to the fiber ends are detected by a light intensity detecting unit, and based on the detected light intensity, a two-dimensional image is acquired.

10. Adaptive optics comprising:

a single wavefront aberration obtaining unit configured to obtain wavefront aberration in return beams returned from an object irradiated by a plurality of measuring beams; and a single wavefront aberration correcting unit configured to correct wavefront aberration in each of the return beams returned from the object irradiated by a plurality of measuring beams, which enter the wavefront aberration correcting unit with different angles, based on the obtained wavefront aberration, wherein the wavefront aberration obtaining unit is disposed at a position optically conjugate with that of the wavefront aberration correcting unit, and obtains a wavefront aberration in one beam of the plurality of return beams, and wherein the single wavefront aberration correcting unit corrects wavefront aberration in each of the return beams based on the obtained wavefront aberration in the one beam.

11. A control method for an optical image acquisition apparatus in which a wavefront of reflected or backscattered beams reflected or backscattered by a surface of an object to be measured when measuring beams including a plurality of beams are scanned on the surface is corrected, and at least an image of the object is acquired, comprising steps of:

projecting the measuring beams including the plurality of beams on a single wavefront aberration correcting unit with different incident angles from each other, respectively, scanning the surface to be measured with the measuring beams reflected by the single wavefront aberration correcting unit by using a scanning unit, obtaining a wavefront aberration in measuring beams reflected or backscattered by the surface to be measured by using a wavefront aberration obtaining unit, and controlling correction of the single wavefront aberration correcting unit, based on the obtained wavefront aberration, wherein the wavefront aberration obtaining unit is disposed at a position optically conjugate with that of the wavefront aberration correcting unit, and obtains a wavefront aberration in one beam of the plurality of return beams, and wherein the single wavefront aberration correcting unit corrects wavefront aberration in each of the return beams based on the obtained wavefront aberration in the one beam.

12. The optical image acquisition apparatus according to claim 1, wherein each of the return beams enters the wavefront aberration correcting unit with different angles.

13. A non-transitory computer readable storage medium that stores a computer program which, when executed by a processor of an optical image acquisition apparatus in which a wavefront of reflected or backscattered beams reflected or backscattered by a surface of an object to be measured when measuring beams including a plurality of beams are scanned on the surface is corrected, and at least an image of the object is acquired, causes the optical image acquisition apparatus to perform the steps of:

projecting the measuring beams including the plurality of beams on a single wavefront aberration correcting unit with different incident angles from each other, respectively, scanning the surface to be measured with the measuring beams reflected by the single wavefront aberration correcting unit by using a scanning unit, obtaining a wavefront aberration in measuring beams reflected or backscattered by the surface to be measured by using a wavefront aberration obtaining unit, and controlling correction of the single wavefront aberration correcting unit, based on the obtained wavefront aberration, wherein the wavefront aberration obtaining unit is disposed at a position optically conjugate with that of the wavefront aberration correcting unit, and obtains a wavefront aberration in one beam of the plurality of return beams, and wherein the single wavefront aberration correcting unit corrects wavefront aberration in each of the return beams based on the obtained wavefront aberration in the one beam.

* * * * *